United States Patent [19]
Yu

[11] Patent Number: 5,226,950
[45] Date of Patent: Jul. 13, 1993

[54] LIQUID-IN-LIQUID SENSOR AND METHOD

[75] Inventor: Ho Yu, Murrysville, Pa.

[73] Assignee: Aluminum Company of America, Pittsburgh, Pa.

[21] Appl. No.: 899,467

[22] Filed: Jun. 16, 1992

[51] Int. Cl.$^5$ .................. C22B 9/05; C22B 21/06
[52] U.S. Cl. .................. 75/387; 73/19.07; 73/61.43; 75/681; 266/80
[58] Field of Search ........... 75/387, 681; 266/80; 73/19.07, 19.01, 19.1, 61.43

[56] References Cited

U.S. PATENT DOCUMENTS

| | | | |
|---|---|---|---|
| 3,262,313 | 7/1966 | Hanna | 73/302 |
| 3,426,584 | 2/1969 | Smith | 73/64.4 |
| 3,765,227 | 10/1973 | Campbell et al. | 73/64.4 |
| 3,767,382 | 10/1973 | Bruno et al. | 75/680 |
| 3,780,568 | 12/1973 | Goldmann et al. | 73/64.4 |
| 3,839,019 | 10/1974 | Bruno et al. | 75/681 |
| 3,849,119 | 11/1974 | Bruno et al. | 75/680 |
| 3,881,344 | 5/1975 | Jobe | 73/64.4 |
| 3,972,709 | 8/1976 | Chia et al. | 75/680 |
| 3,982,913 | 9/1976 | Feichtinger | 55/207 |
| 4,390,364 | 6/1983 | Yu | 75/601 |
| 4,416,148 | 11/1983 | Klus et al. | 73/64.4 |
| 4,731,732 | 3/1988 | Warchol et al. | 73/19.01 |
| 4,987,950 | 1/1991 | Yu | 164/455 |
| 5,029,821 | 7/1991 | Bar-on et al. | 75/681 |
| 5,031,444 | 5/1991 | Doutre et al. | 73/19.07 |

Primary Examiner—Melvyn J. Andrews
Attorney, Agent, or Firm—David W. Pearce-Smith; Douglas G. Glantz

[57] ABSTRACT

The present invention includes process and apparatus for continuously monitoring or detecting a liquid element or compound in another, different liquid including introducing a gas into a first liquid, measuring bubble size of bubble formation of the gas in the first liquid, introducing a second liquid element or compound into the first liquid to form a combination liquid, introducing a gas into the combination liquid, measuring bubble size of bubble formation of the gas in the combination liquid, and comparing gas bubble formation in the first liquid with gas bubble formation in the combination liquid to determine the amount of the second liquid in the combination liquid. The present invention further includes controlling or adjusting the amount of the second liquid contained in the first liquid in response to the monitoring and detecting determination of the present invention.

21 Claims, 3 Drawing Sheets

LIQUID-IN-LIQUID SENSOR AND METHOD

BACKGROUND OF THE INVENTION

1. Field of the Invention

This invention relates to means and method for analyzing the presence of one liquid element or compound in another, different liquid element or compound. In one aspect, the invention relates to method and apparatus for continuously monitoring and controlling the amount of an immiscible liquid element or compound suspended in molten metal. In one aspect, the invention relates to a liquid contaminant sensor for molten metal, e.g., such as method and apparatus for continuously monitoring and controlling the amount of liquid magnesium chloride salts suspended in molten aluminum or aluminum alloys.

2. Background Information

Quality aluminum production requires monitoring and controlling the amount of contaminants or impurities in the aluminum or aluminum alloy. Whether the aluminum production is primary metal (from smelting alumina) or secondary (from recycling), quality aluminum production processes remove impurities such as sodium, calcium, hydrogen, and other trace elements, e.g., such as lithium. Quality aluminum processes require product aluminum containing not more than one part per million of sodium or calcium.

Conventional aluminum purification employs reaction gases to react with the impurities which are more electropositive than aluminum. Fluxing the aluminum or aluminum alloys with reaction gases such as chlorine is a first step in one method for removing hydrogen, sodium, calcium, or other trace elements. Fluxing with chlorine, sometimes called chloridizing, removes hydrogen by diffusion into the gas bubbles and forms contaminant salts of sodium chloride and calcium chloride.

INTRODUCTION TO THE INVENTION

Contaminant salts from chloridizing can cause problems including casting problems and ingot defects called oxide patches which cause problems when rolling the ingot. The presence of these contaminant salts interferes with certain fabrication procedures. Of particular interest to quality aluminum fabrication today is hot rolling operations where any significant amount of these contaminant salts causes severe edge cracking during hot rolling reductions. The edge cracking problem is particularly acute in alloys containing magnesium, e.g., in amounts of about 2 to 10 wt. %.

U.S. Pat. No. 4,390,364, issued to the present inventor Dr. Ho Yu, describes the problem of liquid magnesium chloride particles in thin sheet aluminum 5182 alloy. Aluminum 5182 alloy containing about 4% to 5% magnesium, along with about 0.2% to 0.5% manganese, is used in tear-open beverage can ends. Thin sheets of 5182 alloy are produced by casting relatively large ingot which is homogenized and hot rolled into thick sheet followed by cold rolling into thin sheet. Alloy 5182 is treated to remove sodium and calcium, prior to casting, by chloridizing the aluminum by bubbling chlorine gas through the molten aluminum while it is in a furnace or holding vessel. Magnesium in the chloridized 5182 alloy is converted to $MgCl_2$ in the form of minute liquid particles. These particles can present some difficulty in removal. If substantial amounts of such particles are carried with the metal to the casting operation, the resulting cast ingot can exhibit surface patches of salts and oxides of magnesium and aluminum. These oxide patches cause edge cracking during subsequent rolling. Edge cracking can be so excessive as to impede rolling or to render the ingot unacceptable.

Magnesium in molten aluminum alloys reacts in the chloridizing process to form magnesium chloride. Magnesium in the molten aluminum alloys reacts to chloridizing to form magnesium chloride even though chlorine and aluminum chloride, as the reaction product of chlorine and aluminum, react with sodium preferentially over magnesium at equilibrium conditions. By chemical reaction equilibria and mass action, chlorine reacts first with aluminum and then with magnesium. Chlorine released in an aluminum alloy melt containing magnesium and trace elements of sodium and calcium reacts first with aluminum, which goes off as aluminum chloride vapor at temperatures of molten aluminum metal, and then with magnesium to form liquid magnesium chloride. Subsequently, aluminum chlorides and magnesium chlorides encounter the trace elements of sodium and calcium to form equilibrium products of sodium chloride and calcium chloride.

Sodium chloride and calcium chloride are solids at molten aluminum temperatures and may be filtered from the molten aluminum. Magnesium chloride, on the other hand, is a liquid salt suspended in molten aluminum and does not filter from the molten aluminum through conventional molten metal filters.

Significant amounts of liquid magnesium chloride are suspended in the molten aluminum in unknown quantities.

Typically, molten aluminum is analyzed for magnesium chloride by withdrawing a sample, allowing it to cool and solidify, cutting out a section, and using standard chemical or physical analytical techniques. Such a procedure takes too much time, and the results do not correlate well with a production run as it proceeds with varying conditions. In most cases, production can not be stopped or delayed until an analysis is obtained by such a long analytic procedure.

Quality aluminum production today requires a more timely method for determining the extent of magnesium chloride in molten aluminum. A method is needed to monitor the amount and extent of liquid magnesium chloride in molten aluminum in real time.

Further, magnesium chloride does not dissolve in the molten aluminum to form a homogeneous solution. For this reason, a sample taken from one location may not correspond to the extent of magnesium chloride in aluminum in another part of the production run or at another time in the run.

Campbell et al, U.S. Pat. No. 3,765,227, disclose a continuous analytical determination of minor solute ingredients in solution in liquids. Campbell uses two tubes and measures the maximum differential pressure between two supplies of inert gas to the two tubes. However, liquid particles of magnesium chloride do not dissolve in the molten aluminum to form homogeneous solution.

In accordance with the present invention, method and apparatus have been developed for continuously monitoring and controlling the amount of liquid magnesium chloride in a non-homogeneous suspension in molten aluminum alloy by a novel technique and with novel apparatus employing a single tube for the molten metal analysis.

It is an object of the present invention to provide efficient means and method for monitoring the amount of a first liquid in another, second liquid.

It is a further object of the present invention to provide efficient means and method for controlling the amount of a first liquid in another, second liquid.

It is yet another object of the present invention to provide efficient means and method for monitoring and controlling the amount of an immiscible liquid element or compound suspended in molten metal.

It is yet another object of the present invention to provide efficient means and method for monitoring and controlling the amount of magnesium chloride in molten aluminum.

It is still another object of the present invention to provide efficient means and method for monitoring and controlling the amount of magnesium chloride in molten aluminum through a single tube.

It is still another object of the present invention to provide efficient means and method for automating a sensor system for monitoring and controlling the amount of magnesium chloride in molten aluminum for producing quality aluminum.

These and other objects of the present invention will become apparent from the detailed description which follows.

SUMMARY OF THE INVENTION

The present invention includes process and apparatus for continuously monitoring or detecting a liquid element or compound in another, different liquid including introducing a gas into a first liquid, measuring bubble size of bubble formation of the gas in the first liquid, introducing a second liquid element or compound into the first liquid to form a combination liquid, introducing a gas into the combination liquid, measuring bubble size of bubble formation of the gas in the combination liquid, and comparing gas bubble formation in the first liquid with gas bubble formation in the combination liquid to determine the amount of the second liquid in the combination liquid. The present invention further includes controlling or adjusting the amount of the second liquid contained in the first liquid in response to the monitoring and detecting determination of the present invention.

In one aspect, the present invention includes process and apparatus for continuously monitoring the amount of liquid magnesium chloride suspended in a non-homogeneous molten aluminum alloy including introducing a first inert detecting gas at a predetermined, set pressure into a molten aluminum alloy through a first gas discharge orifice in an upwardly extending tube positioned in a flowing liquid stream of molten aluminum alloy containing molten magnesium metal, measuring detecting gas flow rate and frequency of gas bubble formation of the detecting gas upon detaching from the first discharge orifice and entering into the molten aluminum alloy containing molten magnesium metal, fluxing the molten aluminum alloy with a chlorine-containing gas to form a non-homogeneous suspension of liquid magnesium chloride in molten aluminum alloy, introducing a second inert detecting gas at a predetermined, set pressure into the non-homogeneous suspension through a second gas discharge orifice in an upwardly extending tube positioned downstream from the fluxing, measuring gas flow rate and frequency of gas bubble formation of the second detecting gas upon detaching from the second discharge orifice and entering into the dispersion, comparing the second detecting gas bubble formation with the first detecting gas bubble formation to determine the amount of liquid magnesium chloride suspended in molten aluminum alloy, and adjusting the amount of fluxing chlorine-containing gas to change the amount of liquid magnesium chloride formed and suspended in the molten aluminum alloy.

DETAILED DESCRIPTION

The present invention provides process and apparatus for continuously monitoring a liquid constituent in another, different liquid. The invention operates by providing for the measurement of bubble formation of gas injected into liquid to detect a liquid constituent. The present invention further provides for controlling or adjusting the amount of the liquid constituent in response to the liquid detection determination of the present invention.

In one aspect, the present invention provides process and apparatus for continuously monitoring the amount of liquid magnesium chloride suspended in a non-homogeneous molten aluminum alloy. An inert detecting gas at a predetermined, set pressure is injected into a molten aluminum alloy through a gas discharge orifice in an upwardly extending tube positioned in a flowing liquid stream of the molten aluminum alloy containing molten magnesium metal. The present invention provides for measuring detecting gas flow rate and frequency of gas bubble formation of the detecting gas upon detaching from the first discharge orifice and entering into the molten aluminum alloy containing molten magnesium metal. Fluxing certain aluminum alloys, e.g., such as magnesium-containing aluminum alloys, with a chlorine-containing gas forms a non-homogeneous suspension of liquid magnesium chloride in molten aluminum alloy. Inert detecting gas can be injected at a predetermined, set pressure into the non-homogeneous dispersion of magnesium chloride in molten aluminum through a gas discharge orifice in an upwardly extending tube positioned downstream from a fluxing operation to determine amounts of liquid magnesium chloride in the molten aluminum alloy.

The present invention provides for adjusting the amount of fluxing by chlorine-containing gas to change the amounts of liquid magnesium chloride formed and suspended in the molten aluminum alloy in response to the monitoring and detection determination, thereby providing a continuous monitor and control of the amount of liquid magnesium chloride in the molten aluminum alloy.

The present invention involves the detection in a liquid, e.g., such as in a molten metal, of surface interfacial chemical forces attributable to the presence of another, immiscible liquid constituent, e.g., such as molten salt or other liquid contaminants residing in the molten metal.

In the case of immiscible contaminant constituents, surface tension of the molten metal essentially does not change, but reductions of bubble sizes occur because of interfacial chemical forces attributable to contamination by the immiscible constituents onto the bubble.

Reductions or increases of the sizes of the gas bubble in the molten metal can be measured in a continuous manner by a method and apparatus incorporating inert gas flowing through an inverted tube into the molten metal.

By measuring the magnitude of change of the gas bubble, the amount of molten salt can be quantified. By monitoring the inert gas flow rate and frequency of bubble formation (by monitoring the slight tube pressure fluctuation when a bubble is detached from the tube), the bubble size of the inert gas can be determined. The size of the inert gas bubble is related to the contamination by molten salt, and the magnitude of the molten-metal/salt surface interfacial chemical forces can be determined.

Surface interfacial force is the amount of energy needed to create a new surface. The free energy of the gas bubble can be related to gas bubble size and the surface interfacial chemical forces.

Change in Bubble Free Energy = Change in Bubble Surface Area      (1)

$$\Delta G^s = \Delta A(\gamma_{LS} - \gamma_{VS}) + \Delta A \gamma_{LV} \cos\theta \quad (2)$$

where
$\Delta G^S$ = bubble free energy change,
$\Delta A$ = bubble surface area change,
$\gamma_{LS}$ = surface interfacial chemical force between liquid and contacting solid surface,
$\gamma_{VS}$ = surface interfacial chemical force between vapor and contacting solid surface,
$\gamma_{LV}$ = surface interfacial chemical force between liquid and vapor, and
$\theta$ = the angle of detachment of the gas bubble from the solid discharge orifice, as measured from the horizontal.

$$\Delta G^S/\Delta A = \gamma_{LS} - \gamma_{VS} + \gamma_{LV}\cos\theta \quad (3)$$

At equilibrium:

$$\lim_{\Delta A \to 0} \Delta G^S/\Delta A = \delta G^S/\delta A = 0 \quad (4)$$

A sum of the forces in the horizontal direction correlates the elements of surface interfacial chemical forces.

$$\gamma_{LS} - \gamma_{VS} + \gamma_{LV}\cos\theta = 0 \quad (5)$$

$$\gamma_{LS} = \gamma_{VS} - \gamma_{LV}\cos\theta = 0 \quad (6)$$

Bubble angle, Theta, decreases as wettability increases. For example, a discharge orifice rim of a material such as boron nitride is not wetted by molten aluminum and has a high angle of bubble attachment. Stainless steel, on the other hand, is wetted by molten aluminum and results in a low angle of bubble attachment (flat bubble), for the same discharge orifice diameter and wall thickness.

A sum of the forces in the vertical direction defines a further relationship of surface interfacial chemical force.

Buoyancy Force + Flow Inertia = Liquid/Solid Attachment      (7)

$$V_B(\rho_{alloy} - \rho_{argon}) + \tfrac{1}{2}\rho\mu^2 = 2\pi r_{rim}\gamma_{VS} \quad (98)$$

Density of the argon gas is negligible in view of the density of the aluminum alloy metal.

$$V_B(\rho_{alloy}) + \text{Flow inertia} = 2\pi r_{rim}\beta_{LS} \quad (9)$$

$$\text{Flow inertia} \approx \tfrac{1}{2}\rho\mu^2 = \tfrac{1}{2}\rho(s \cdot cm^3/\pi r^2)^2 \quad (10)$$

The temperature dependence of the surface interfacial chemical force relationship can be correlated by equation (11).

$$\gamma = \gamma^O(1 - T/T_c) \quad (11)$$

Figure 1:
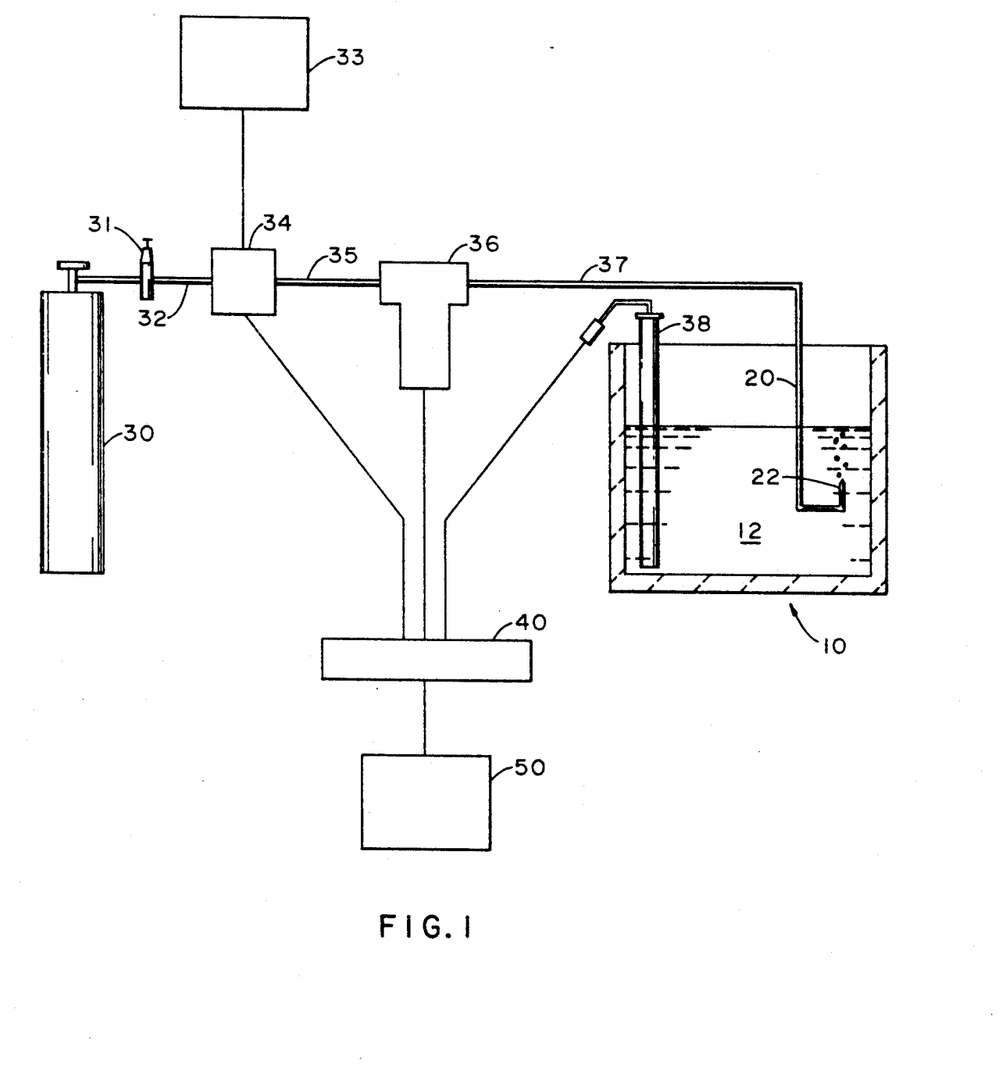
FIG. 1 depicts a process schematic for a liquid-in-liquid sensor in accordance with the present invention.

Where
$T_c$ = critical temperature (surface interfacial chemical force goes to zero), and
$\gamma^O$ = reference surface interfacial chemical force Referring now to FIG. 1, a vessel 10 for containing molten metal such as molten aluminum alloy metal at a temperature of above about 1300° F. contains molten aluminum alloy 12. Tube 20 having an internal diameter of about ⅛ inch and made of ceramic, e.g., such as boron nitride, or of stainless steel tubing projects into molten aluminum alloy 12. Tube 20 is adapted to terminate in upwardly extending gas discharge end 22. Bubble forming gas is discharged, as shown, into the molten aluminum through the tubing orifice formed by discharge end 22.

Bubble-forming gas, e.g., such as an inert gas such as argon, is supplied from gas tank or reservoir 30 and controlled by tank valve and pressure regulator 31 which permits gas to flow out of tank 30 through line 32 to flow control module 34. Flow controller 33 controls flow module unit 34 to provide for an essentially steady-state gas flow rate and to provide consistent and regular bubble formation size and frequency. The detecting gas flows from flow module 34 through line 35. Pressure of the gas is set at a predetermined, set pressure. Slight variations (e.g., on the order of about 0.5 psia) in the predetermined, set pressure are monitored by pressure transducer 36. Gas flowing in line 37 is passed to tube 20 for discharge through tube end 22 into the molten aluminum. Thermocouple 38 measures the temperature in molten aluminum 12. The temperature affects surface interfacial chemical forces in an inverse linear relationship, and bubble size should be corrected because of temperature changes. Data from flow module 34, pressure transducer 36, and thermocouple 38 are received and recorded by data logger unit 40. Data from data logger 40 is received and correlated at computer 50.

A plot of bubble formation by computer 50 presents the frequency of bubble formation of the inert gas discharging through discharge end 22 into the molten aluminum. Frequency of bubble formation is presented by plotting the slight variations in the predetermined, set pressure (e.g., 2–3 psia). Bubble size of bubble formation then is calculated from detecting gas flow rate and frequency of bubble formation.

Figure 2:
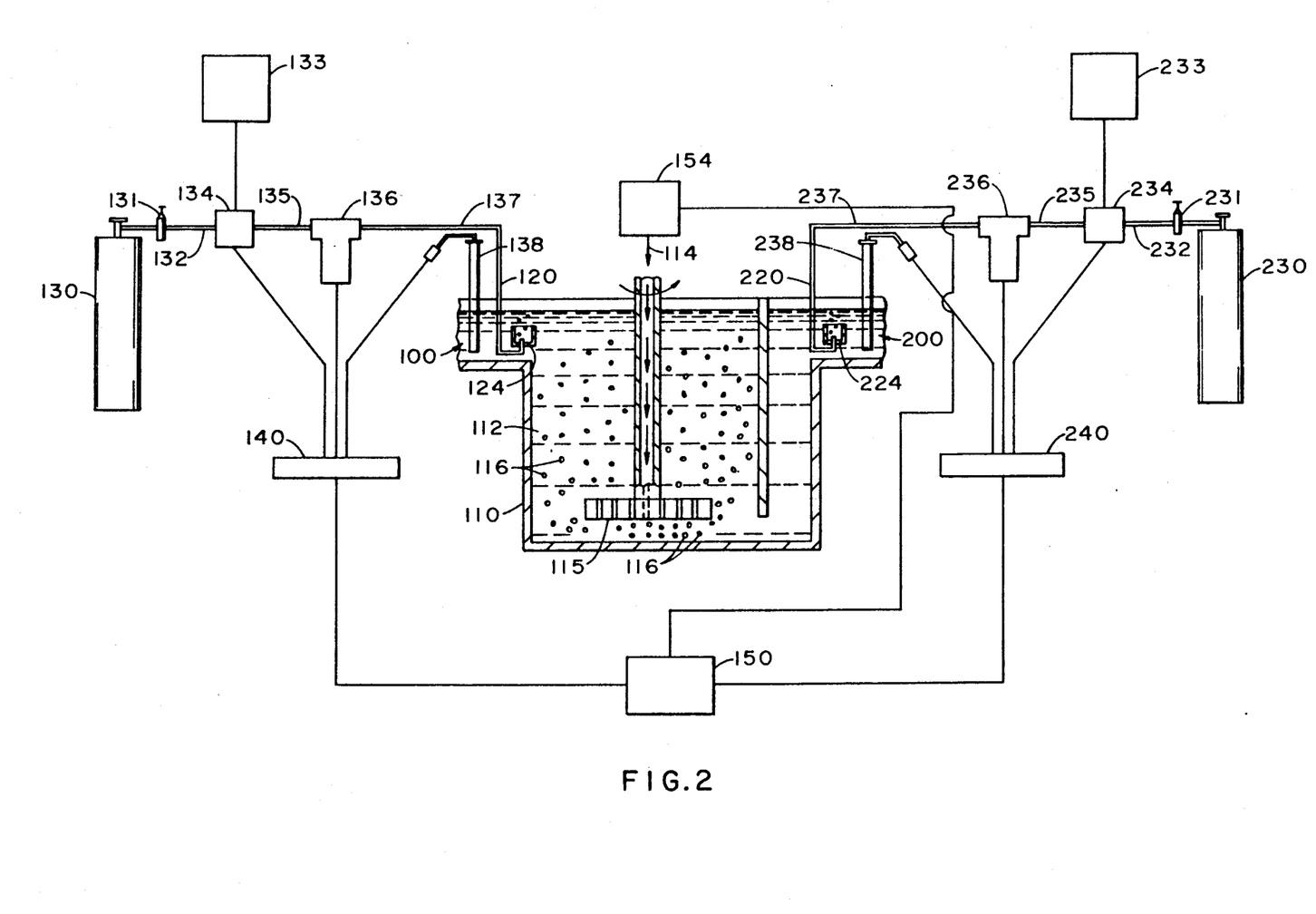
FIG. 2 shows a process schematic in accordance with the present invention as applied to a flowing liquid stream.

FIG. 2 shows a process schematic in accordance with the present invention as applied to a flowing liquid stream 100 entering vessel 110 for fluxing molten metal such as molten aluminum alloy 112 at a temperature of above about 1300° F. with a fluxing gas mixture. Fluxing gas, e.g., such as chlorine or mixtures of chlorine and inert gas, are passed to vessel 110 through fluxing gas feed stream 114. Fluxing gas is distributed into the aluminum alloy melt through rotating vane disperser 115. Fluxing gas bubbles enter the aluminum alloy melt as gas bubbles 116. Fluxed molten metal exits fluxing vessel 110 at effluent stream 200.

Tube 120 having an internal diameter of about ⅛ inch made of ceramic, e.g., such as boron nitride, or of stainless steel tubing, projects into feed stream 100. Tube 120 is adapted to terminate in upwardly extending gas discharge end as shown by reference numeral 22 in FIG. 1. Bubble forming gas is discharged into the molten aluminum through the tubing orifice formed at the discharge end.

A protective covering, in the shape of a cup-like design, is positioned around the discharge end or discharge orifice of the detecting gas discharge tube as shown by reference numeral 124 for tube 120 and by protective cover 224 for tube 220. The protective cover can be made of a material resistant to the effects of molten metal, e.g., a material such as a carbon graphite. The protective cover shields the discharge orifice from the effects of flowing metal and reduces disturbance to the gas bubble detaching from the detecting gas discharge orifice of the present invention.

Tube 220 of ceramic or stainless steel tubing having an internal diameter of about ⅛ inch projects into exit stream 200. Tube 220 is adapted to terminate in upwardly extending gas discharge end as shown by reference numeral 22 in FIG. 1. Bubble forming gas is discharged into the molten aluminum through the tubing orifice formed at the discharge end.

Bubble-forming detecting gas, e.g., such as an inert gas such as argon, is controllably supplied to detecting gas discharge tube 120 and, separately, to detecting gas discharge tube 220. Detecting gas is controllably supplied from a gas tank or reservoir controlled by tank valve and pressure regulator through a flow control module. A flow controller controls the flow module unit to provide for an essentially steady-state gas flow rate and to provide consistent and regular bubble formation size and frequency. The detecting gas flows into detecting gas discharge tubes at a pressure of the gas set at a predetermined, set pressure. Slight variations (e.g., on the order of about 0.5 psia) in the predetermined, set pressure are monitored by a pressure transducer. Detecting gas is passed to tube 120 and, separately, to tube 220 for discharge through each respective tube end into the molten aluminum.

A thermocouple measures the temperature in molten aluminum at the proximate location of the detecting gas discharge tube. The temperature affects surface interfacial chemical forces in an inverse linear relationship as shown in equations (11) and (12), supra, and bubble size should be corrected because of temperature changes.

The fluxing operation produces a cooling effect on the aluminum alloy, and the temperature change alters the surface interfacial chemical force. Accordingly, the changes in temperature must be factored into any comparison of change between detecting gas discharge tube 120 in the inlet stream to fluxing unit 110 and detecting gas discharge tube 220 in the outlet stream of fluxing unit 110. For example, the temperature change through the fluxing unit typically can reduce the temperature in the aluminum alloy melt from about 1350° F. to about 1260° F.

$$\gamma_{1350} = \gamma^*(1 - (1350 + 460)/T_c) \quad (12)$$

$$\gamma_{1260} = \gamma^*(1 - (1260 + 460)/T_c) \quad (13)$$

$$\frac{\gamma_{1350}}{\gamma_{1260}} = \frac{(T_c - (1350 + 460) \, °R)}{(T_c - (1260 + 460) \, °R)} \quad (14)$$

Data from the flow module, the pressure transducer, and the thermocouple are received and recorded by data logger units 140 and 240. Data from the data loggers are received and correlated at computer 150 for each of detecting gas discharge tubes 120 and 220.

A plot of bubble formation by computer 150 can provide the frequency of bubble formation of the inert gas discharging through discharge tube 120 and discharge tube 220 into the molten aluminum. Frequency of bubble formation is provided by plotting the slight variations in the predetermined, set pressure (e.g., 2-3 psia). Bubble size of bubble formation then is calculated from detecting gas flow rate and frequency of bubble formation. The fluxing gas flow rate is monitored and adjusted in response to the computer 150 comparison of analyses received from upstream detecting gas discharge tube 120 and downstream detecting gas discharge tube 220, as discussed in relation to FIG. 3.

Figure 3:
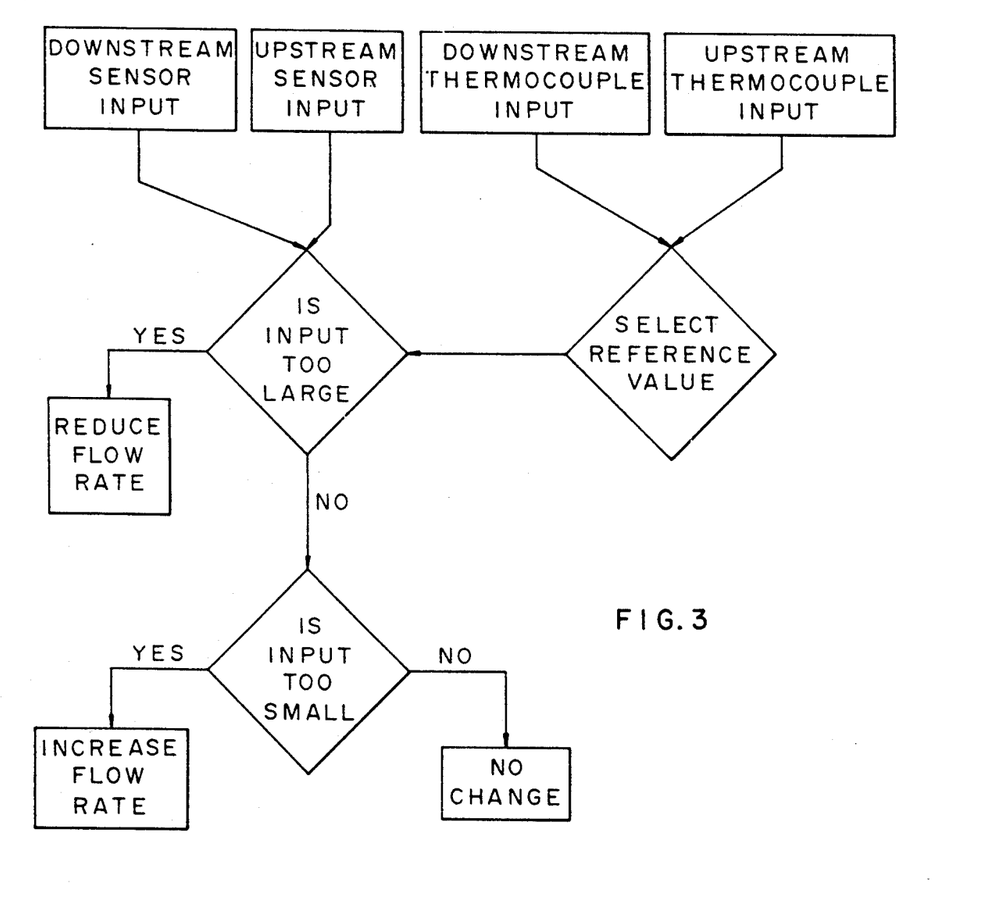
FIG. 3 depicts a logic and process flow diagram showing decisions of the process in controlling the flow of fluxing reaction gas into aluminum alloy in accordance with the present invention.

FIG. 3 presents a logic and process flow diagram showing decisions of the process for controlling the flow of fluxing reaction gas into aluminum alloy in accordance with the present invention. Essentially, the procedure followed in the process includes the steps of inputting the sensor signals from the two detectors into the microprocessor, comparing the sensor signals and determining if the difference is larger than the reference value stored in the microprocessor, while factoring in the temperature value coming in from the thermocouple positioned at the location with the source of each sensor signal. If the comparison is larger than the reference signal, a command signal is sent to a flow rate module 154 to reduce the flow rate of chloridizing gas 114 to fluxing unit 110 as shown in FIG. 2. If the comparison is not larger than the reference signal, the microprocessor determines if the comparison is smaller than the reference value, and if so, a command signal is sent to the flow control module 154 to increase flow rate. If the input signal is not smaller than the reference signal, no command signal is sent to flow module 154.

The present invention provides a real-time, in-line sensor for detecting and monitoring one liquid constituent in another, different liquid.

The present invention provides a contaminant sensor for monitoring and controlling molten salt generation in the fluxing process for removing impurities from molten aluminum or aluminum alloys and thus provides for the production of quality aluminum ingot having reduced or eliminated ingot oxide patch defects.

EXAMPLE

This actual example was conducted using bench scale apparatus as depicted by the process schematic shown in FIG. 1. A molten metal sample of about fifty (50) pounds was placed in the containment vessel 10 of FIG. 1. Argon was used as the detecting gas of the present invention, and detecting gas flow rates through flow module 34 were measured in units of standard cubic feet per hour (SCFH). Molten metal samples of aluminum, aluminum with varying amounts of impurity elements or compounds, aluminum 5182 alloy, and aluminum 5182 alloy with varying amounts of impurity elements or compounds were analyzed by the present invention. "Al 5182 alloy" represents aluminum containing about 0.30–0.47 wt. % manganese and about 4.35–4.80 wt. % magnesium. Certain samples were fluxed with a fluxing mixture gas of argon-90%, chlorine-10%. Flow rates of detecting gas (in standard cubic feet per hour) and bubble frequency (in rate per minute) were monitored, and bubble size calculated. Results are presented in the following Table.

TABLE

| Run | Sample (% = wt. %) | Detecting Gas Flow (SCFH) | Temp. (°F.) | Bubble Frequency | Bubble Size ($cm^3$) |
|---|---|---|---|---|---|
| 1 | Aluminum (Al) | 0.2 | 1297 | 126–130 | 0.7 |
| 2 | Al + 0.06% $MgCl_2$ | 0.2 | 1296 | 96–97[1] | 1.0 |
| 3 | Al 5182 alloy | 0.2 | 1288 | 138–140 | 0.7 |
| 4 | 5182 + 0.04% $MgCl_2$ | 0.2 | 1291 | 164–165 | 0.6 |
| 5 | 5182 + 0.08% $MgCl_2$ | 0.2 | 1299 | 179–180 | 0.5 |
| 6 | 5182 + 0.08% $MgCl_2$ | 0.1 | 1309 | 86–88 | 0.5 |
| 7 | 5182 + 0.12% $MgCl_2$ | 0.1 | 1301 | 139–141 | 0.3 |
| 8 | Al 5182 alloy | 0.3 | 1297 | 134–136 | 1.0 |
| 9 | 5182 + 0.014% Ca | 0.1 | 1289 | 134–136 | .35 |
| 10 | 5182 + 0.014% Ca, 0.1% Na | 0.1 | 1347 | 174–176 | .27 |
| 11 | 5182 + 0.014% Ca, 0.1% Na fluxed with Ar + Cl | 0.1 | 1306 | 120–122[1] | 0.4 |
| 12 | Al 5182 alloy | 0.2 | 1295 | 94–97 | 1.0 |
| 13 | 5182 + 0.1% Ca | 0.2 | 1294 | 84–86 | 1.1 |
| 14 | 5182 + 0.1% Ca fluxed (Ar + Cl 5 min.) | 0.2 | 1286 | 102–104 | 0.9 |
| 15 | 5182 + 0.1% Ca fluxed (Ar + Cl 10 min.) | 0.2 | 1296 | 150–152 | 0.6 |
| 16 | 5182 + 0.1% Ca fluxed (Ar + Cl 15 min.) | 0.2 | 1300 | 160 | .59 |
|  |  | 0.2 | 1302 | 168 | .56 |
|  |  | 0.2 | 1303 | 168 | .56 |
|  |  | 0.2 | 1303 | 168 | .56 |
|  |  | 0.2 | 1306 | 172 | .54 |
|  |  | 0.2 | 1307 | 180 | .52 |

Note[1] Oxides were formed and dispersed into the metal. Oxides increase bubble size.

The apparatus and method of the present invention are not limited to the descriptions of specific embodiments hereinabove, but rather the apparatus and method of the present invention should be viewed in terms of the claims that follow and equivalents thereof.

What is claimed is:

1. A method for detecting a liquid constituent in another liquid comprising:
   (a) introducing a substantially inert gas into a first liquid element or compound;
   (b) measuring bubble size of bubble formation of said gas in said first liquid;
   (c) introducing a second liquid element or compound into said first liquid to form a combination liquid;
   (d) introducing a substantially inert gas into said combination liquid;
   (e) measuring bubble size of bubble formation of said gas in said combination liquid; and
   (f) comparing said gas bubble size of bubble formation in said first liquid with said gas bubble size of bubble formation in said combination liquid to form a determination of the amount of second liquid element or compound in said combination liquid.

2. A method as set forth in claim 1, wherein said introducing inert gas comprises measuring gas flow rate and bubble frequency to determine said bubble size.

3. A method as set forth in claim 2, wherein said introducing inert gas comprises discharging said gas through an upwardly extending tube having a gas discharge orifice adapted for producing said bubble formation.

4. A method as set forth in claim 3, further comprising adjusting the amount of introducing said second liquid element or compound into said first liquid to form a combination liquid in response to said determination of amount of said second liquid element or compound in said combination liquid to change said amount of said second liquid element or compound in said combination liquid.

5. A method as set forth in claim 4, wherein said first liquid comprises molten metal and said second liquid comprises liquid metal salt.

6. A method as set forth in claim 5, wherein said molten metal comprises molten aluminum or aluminum alloy and said liquid metal salt comprises liquid magnesium chloride.

7. A method as set forth in claim 6, wherein said liquid magnesium chloride is formed by fluxing molten aluminum alloy containing magnesium with a chlorine-containing gas to form magnesium chloride.

8. A method for continuously monitoring the amount of one liquid constituent another, different liquid comprising:
   (a) introducing a substantially inert gas into a first liquid element or compound at a first location in a flowing liquid stream;
   (b) measuring bubble size of bubble formation of said gas upon entering said first liquid;
   (c) introducing an second liquid element or compound into said first liquid to form a combination liquid;
   (d) introducing a substantially inert gas into said combination liquid at a second location downstream from said combination liquid formation in said flowing liquid stream;
   (e) measuring bubble size of bubble formation of said gas upon entering said combination liquid; and
   (f) comparing said second location gas bubble size with said first location gas bubble size to form a determination of the amount of said second liquid in said combination liquid.

9. A method as set forth in claim 8, wherein said introducing inert gas comprises measuring gas flow rate and bubble frequency to determine said bubble size.

10. A method as set forth in claim 9, wherein said introducing inert gas comprises discharging said gas through an upwardly extending tube having a gas discharge orifice adapted for producing said bubble formation.

11. A method as set forth in claim 10, further comprising protecting said orifice from flow disturbances in said molten aluminum alloy.

12. A method as set forth in claim 11, wherein said protecting said orifice from flow disturbances is said molten aluminum comprises establishing protective carbon/graphite walls around said upwardly extending tube to reduce flow disturbances in said molten aluminum alloy.

13. A method as set forth in claim 11, wherein said molten aluminum alloy comprises aluminum can sheet alloy.

14. Apparatus for detecting one liquid in another liquid comprising:
   (a) a liquid container;
   (b) a first detecting gas discharge orifice in said liquid container;
   rate and frequency of gas
   (c) means for measuring gas flow bubbles forming at said first detecting gas discharge orifice and detaching therefrom;
   or
   (d) means for introducing a second liquid element compound into said first liquid container;
   (e) a second detecting gas discharge orifice in said liquid container;
   (f) means for measuring gas flow rate and frequency of gas bubbles forming at said second detecting gas discharge orifice and detaching therefrom; and
   (g) means for comparing said second detecting gas flow rate and bubble frequency with said first detecting gas flow rate and bubble frequency to determine the amount of said second liquid in said first liquid.

15. Apparatus as set forth in claim 14, wherein said first and second detecting gas discharge orifices comprise upwardly extending tubes having an orifice adapted to produce said bubble formation and positioned in a lower portion in said liquid container.

16. Apparatus as set forth in claim 15, further comprising means for protecting said detecting gas discharge orifices from liquid flow disturbances in said liquid container.

17. Apparatus as set forth in claim 16, wherein said liquid comprises molten aluminum or aluminum alloy, said apparatus further comprising means for introducing reactive gas into said liquid container for fluxing said molten aluminum or aluminum alloy with chlorine-containing gas.

18. Apparatus as set forth in claim 17, wherein said means for protecting said detecting gas discharge orifices from liquid flow disturbances comprises at least one protective carbon/graphite wall adjacent said upwardly extending tubes composed of stainless steel to reduce flow disturbances in said molten aluminum or aluminum alloy.

19. Apparatus as set forth in claim 18, wherein said liquid container comprises a trough for containing a flowing stream of molten aluminum alloy.

20. Apparatus as set forth in claim 19, wherein said first detecting gas discharge orifice is positioned upstream of said fluxing means for introducing reactive gas in said trough for containing a flowing stream of molten aluminum alloy and said second detecting gas discharge orifice is positioned downstream from said fluxing means for introducing reactive gas in said trough for containing a flowing stream of molten aluminum alloy.

21. A process for continuously controlling the amount of liquid magnesium chloride in a non-homogeneous dispersion in molten aluminum alloy comprising:
   (a) introducing a first inert detecting gas at a predetermined, set pressure into a molten aluminum alloy through a first gas discharge orifice in an upwardly extending tube positioned in a flowing liquid stream of molten aluminum alloy containing molten magnesium metal;
   (b) measuring detecting gas flow rate and gas bubble formation frequency of said detecting gas upon detaching from said first discharge orifice and entering into said molten aluminum alloy containing molten magnesium metal;
   (c) fluxing said molten aluminum alloy with a chlorine-containing gas to form a non-homogeneous dispersion of liquid magnesium chloride in molten aluminum alloy;
   (d) introducing a second inert detecting gas at a predetermined, set pressure into said non-homogeneous dispersion through a second gas discharge orifice in an upwardly extending tube positioned downstream from said fluxing;
   (e) measuring detecting gas flow rate and gas bubble formation frequency of said second detecting gas upon detaching from said second discharge orifice and entering into said dispersion;
   (f) comparing said second detecting gas flow rate and bubble frequency with said first detecting gas flow rate and bubble frequency to determine the amount of said liquid magnesium chloride in said molten aluminum alloy; and
   (g) adjusting the amount of said fluxing chlorine-containing gas to change said amount of said liquid magnesium chloride in said molten aluminum alloy.

* * * * *

UNITED STATES PATENT AND TRADEMARK OFFICE
CERTIFICATE OF CORRECTION

PATENT NO. : 5,226,950
DATED : July 13, 1993
INVENTOR(S) : Ho Yu

It is certified that error appears in the above-indentified patent and that said Letters Patent is hereby corrected as shown below:

| | |
|---|---|
| Col. 11, line 9<br>Claim 14 | Delete "rate and frequency of gas". |
| Col. 11, line 10<br>Claim 14 | After "flow", insert --rate and frequency of gas--. |
| Col. 11, line 13<br>Claim 14 | delete "or". |
| Col. 11, line 15<br>Claim 14 | After "element", insert --or--. |

Signed and Sealed this

Seventh Day of June, 1994

Attest:

BRUCE LEHMAN

*Attesting Officer*   *Commissioner of Patents and Trademarks*